(12) United States Patent
Fair et al.

(10) Patent No.: US 8,247,597 B2
(45) Date of Patent: Aug. 21, 2012

(54) CONTINUOUS PRODUCTION OF DMAEA QUATERNARY SALTS

(75) Inventors: Barbara E. Fair, Lisle, IL (US); Peter E. Reed, Plainfield, IL (US); Leonard M. Ver Vers, Downers Grove, IL (US); Larry E. Brammer, Jr., Kingsport, TN (US); Charles J. Holada, LaGrange Park, IL (US); Cheng-Sung Huang, Naperville, IL (US); Kailas B. Sawant, Aurora, IL (US)

(73) Assignee: Nalco Company, Naperville, IL (US)

( * ) Notice: Subject to any disclaimer, the term of this patent is extended or adjusted under 35 U.S.C. 154(b) by 330 days.

(21) Appl. No.: 12/691,159

(22) Filed: Jan. 21, 2010

(65) Prior Publication Data

US 2011/0178327 A1    Jul. 21, 2011

(51) Int. Cl.
*C07C 69/52* (2006.01)

(52) U.S. Cl. .......... 560/222

(58) Field of Classification Search .......... None
See application file for complete search history.

(56) References Cited

U.S. PATENT DOCUMENTS

| | | | |
|---|---|---|---|
| 6,683,203 B2 * | 1/2004 | Druzkowski et al. | 560/222 |
| 2011/0021808 A1 * | 1/2011 | Nair et al. | 560/222 |

FOREIGN PATENT DOCUMENTS

| | | |
|---|---|---|
| CN | 1276367 | 12/2000 |
| CN | 1296942 | 5/2001 |
| CN | 201424446 Y | 3/2010 |
| EP | 1 104 400 B1 | 10/2003 |
| JP | 1995/206790 | 8/1995 |
| JP | 2003/342244 | 12/2003 |
| JP | 2004/010508 | 1/2004 |
| JP | 2004/155669 | 6/2004 |

* cited by examiner

*Primary Examiner* — Sudhakar Katakam
(74) *Attorney, Agent, or Firm* — Benjamin E. Carlsen; Andrew D. Sorenson

(57) ABSTRACT

The invention provides a method of continuously producing high quality quaternized N,N-dialkylaminoethyl (meth)acrylates (DMAEA.MCQ) that has a long shelf life and which is stable in water. The method involves placing starting materials into a continuously stirred tank reactor in the presence of less than 6% water. This low amount of water causes two liquid phases to form and prevents unwanted side reactions. The denser liquid phase contains DMAEA.MCQ and the lighter phase contains the starting materials. Liquid from the denser phase is removed from a position where little of the lighter phase has been mixed in. The removed liquid then has any last traces of the starting materials reacted into DMAEA.MCQ and strips away any starting materials with a gas flow. The resulting liquid is high purity DMAEA.MCQ. Water can then safely be added to ease in the transport and use of the produced DMAEA.MCQ.

17 Claims, 2 Drawing Sheets

CONTINUOUS PRODUCTION OF DMAEA QUATERNARY SALTS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to a method and apparatus for the continuous production of quaternized N,N-dialkylaminoethyl (meth)acrylates (DMAEA.MCQ). DMAEA.MCQDMAEA.MCQ is an important monomer intermediate used in producing cationic flocculant polymers. It is known that DMAEA.MCQ can be produced by reacting N,N-dimethylaminoethyl acrylate (DMAEA) under various conditions. A good method of synthesizing DMAEA is described in U.S. patent application Ser. No. 12/468,585. An efficient method of producing DMAEA.MCQ from DMAEA would involve a continuous synthesis, which avoids the burdensome and costly start and stop mechanics inherent in batch type production methods.

A number of unsatisfactory methods have previously been developed to produce DMAEA.MCQ from DMAEA. Japanese Patent Applications 2003/342244, 2004/010508, and 2004/155669 use continuously stirred tank reactors (CSTR) connected in series to continuously produce DMAEA.MCQ. Their preference for multiple reactors however is cumbersome and expensive. Japanese patent application 1995/206790 describes conducting the synthesis in a thin film evaporator reactor. This method unfortunately uses equipment that is typically associated with higher operating costs in comparison with the present invention. U.S. Pat. No. 6,683,203 uses a rotating disc agitated column design but suffers from an unduly long residence time. Chinese patent applications CN 1296942 and CN 1276367 use tower reactors to produce DMAEA.MCQ but are also less than ideal.

Thus there is clear need and utility for an improved method of continuously and efficiently producing DMAEA.MCQ. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment of the invention is directed towards a method of continuously producing QAP. The method comprises the steps of:

continuously feeding reactants into a CSTR, the reactants comprising TAS, water, and an alkylating agent;

maintaining conditions in the CSTR such that two substantially distinct liquid phases form, a first phase and a second phase, the second phase being denser than the first phase, the second phase substantially comprising more than 80% QAP and less than 20% water, the first phase present at greater than about 5 wt. % of the reaction mixture, and substantially comprising TAS, and alkylating agent;

not allowing the water content of the CSTR to exceed 16% of the reactants continuously added to the CSTR; and continuously removing substantially, only second phase liquid from the CSTR.

The method of claim 1 wherein the TAS is selected from the group consisting of:

DMAEA, any n,n-dialkylaminoalkyl (meth)acrylates, (meth)acrylamides, and any combination thereof.

One or more additional embodiments are directed towards this method in which:

The QAP produced may be DMAEA.MCQ. The alkylating group may be selected from the group consisting of: methyl chloride, benzyl chloride, cetyl chloride, dimethyl sulfate, and any other commonly known alkylating agent, and any combination thereof. The TAS may be added to the CSTR from the top of the CSTR. The second phase may be removed from the CSTR from the bottom of the CSTR. Additional reaction of residual TAS in the removed second phase may be facilitated by reacting it in a plug flow reactor and/or by adding additional alkylating agent. The alkylating agent may be removed by purging the second phase liquid with a gas flow. The alkylating agent may be removed by passing it through a stripping column. The alkylating agent may be removed by passing it into the top of a stripping column and passing a gas into the bottom of the stripping column, the gas selected from the list consisting of: air, nitrogen, argon and any combination thereof. The temperature in the CSTR may be maintained at between 40-60° C. The residence time in the CSTR may range between 30-120 minutes. The pressure in the CSTR may be maintained at 30-100 psi. The ratio of first phase to second phase may be maintained at between 1:1 and 1:20. The second phase liquid may be removed from the CSTR at a location in which shear induced mixing of TAS and QAP is low relative to other locations within the CSTR. The method may further comprise the step of adding BHT, copper, MEHQ, and any combination thereof to the produced QAP. The produced QAP may have less than 300 ppm of TAS within it. The method may further comprise the steps of facilitating the reaction of any residual TAS in the second phase liquid;

stripping the alkylating agent from the second phase liquid; and adding water to the second phase liquid to obtain desired physical properties.

BRIEF DESCRIPTION OF THE DRAWINGS

A detailed description of the invention is hereafter described with specific reference being made to the drawings in which.

DETAILED DESCRIPTION OF THE INVENTION

Definitions

For purposes of this application the definition of these terms is as follows:

"BHT" means a molecule according to the formula:

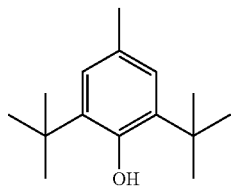

"Continuous Process" means an ongoing chemical process, which is capable of being run continuously over an unlimited period of time in which reagents can be constantly fed into a reaction operation to continually produce product. Continuous Process and Batch Process are mutually exclusive.

"CSTR" means continuously stirred tank reactor.

"DMAEA" means N,N-dimethylaminoethyl acrylate

"DMAEA.MCQ" means quaternized N,N-dialkylaminoethyl acrylates.

"DMAEM" means N,N-dimethylaminoethyl (meth)acrylate

"DMAEA.MCQ" means quaternized N,N-dialkylaminoethyl (meth)acrylates.

"Percent" or "%", unless otherwise stated, means weight percent.

"MEQH" means a molecule according to the formula:

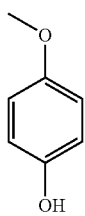

"TAS" means tertiary amine substrate.

"QAP" means quaternary amine product.

In the event that the above definitions or a definition stated elsewhere in this application is inconsistent with a meaning (explicit or implicit) which is commonly used, in a dictionary, or stated in a source incorporated by reference into this application, the application and the claim terms in particular are understood to be construed according to the definition in this application, and not according to the common definition, dictionary definition, or the definition that was incorporated by reference.

Recital

Figure 1:
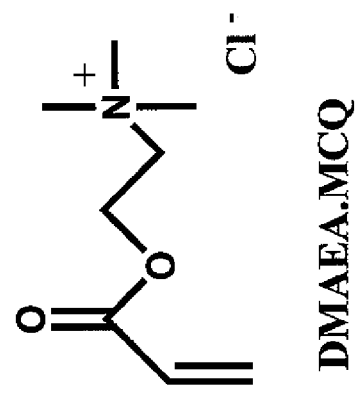
FIG. 1 illustrates the inventive alkylation reaction.
Figure 1:
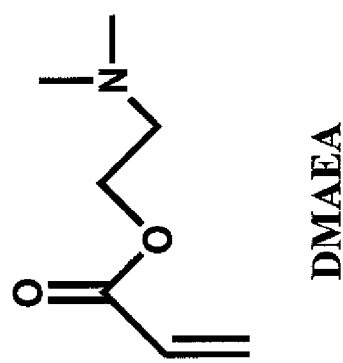

In at least one embodiment, an alkylation reaction is used to produce an alkylated quaternary amine salt from a tertiary amine substrate. This alkylation reaction is facilitated by an alkylating agent. In at least one embodiment, the TAS is one selected from those listed in U.S. patent application Ser. No. 12/468,585. As illustrated in FIG. 1, in at least one embodiment, the tertiary amine substrate is DMAEA, and it is alkylated by the alkylating agent methyl chloride to form the QAP quaternary amine salt DMAEA.MCQ. In at least one embodiment the TAS is DMAEM and the QAP it forms is the quaternary amine salt DMAEM.MCQ.

One major utility inherent in the inventive reaction is that it allows water to be present in the final product while at the same time inhibiting the presence of impurities. Because of the reactive nature of the aminoacrylate substrate, side reactions such as hydrolysis, polymerization, and other reactions can occur at such a rate that impurities accumulate in large enough quantities to negatively impact the quality of the product. Because these side reactions are promoted by water, one approach to prevent such side reactions would be to conduct the reaction in a water free environment. Such a strategy however is frustrated by the physical properties of QAPs such as DMAEA.MCQ and DMAEM.MCQ. Specifically, these QAPs have a lower than desired solubility. They can comprise no more than about 80% of a solution or else they precipitate out of solution when exposed to cold weather during transport. When precipitated out of solution, the QAPs become much harder to store, transport, and pump. These difficulties are avoided in the inventive method, which allows for the presence of water without undue impurities in the reaction product.

In at least one embodiment, the alkylation reactant is selected from the group consisting of: methyl chloride, benzyl chloride, cetyl chloride, dimethyl sulfate, and any other commonly known alkylating agent, and any combination thereof.

In at least one embodiment, the tertiary amine substrate (TAS) is selected from the group consisting of DMAEA, any N,N-dialkylaminoalkyl (meth)acrylates, (meth)acrylamides, and any combination thereof.

Figure 2:
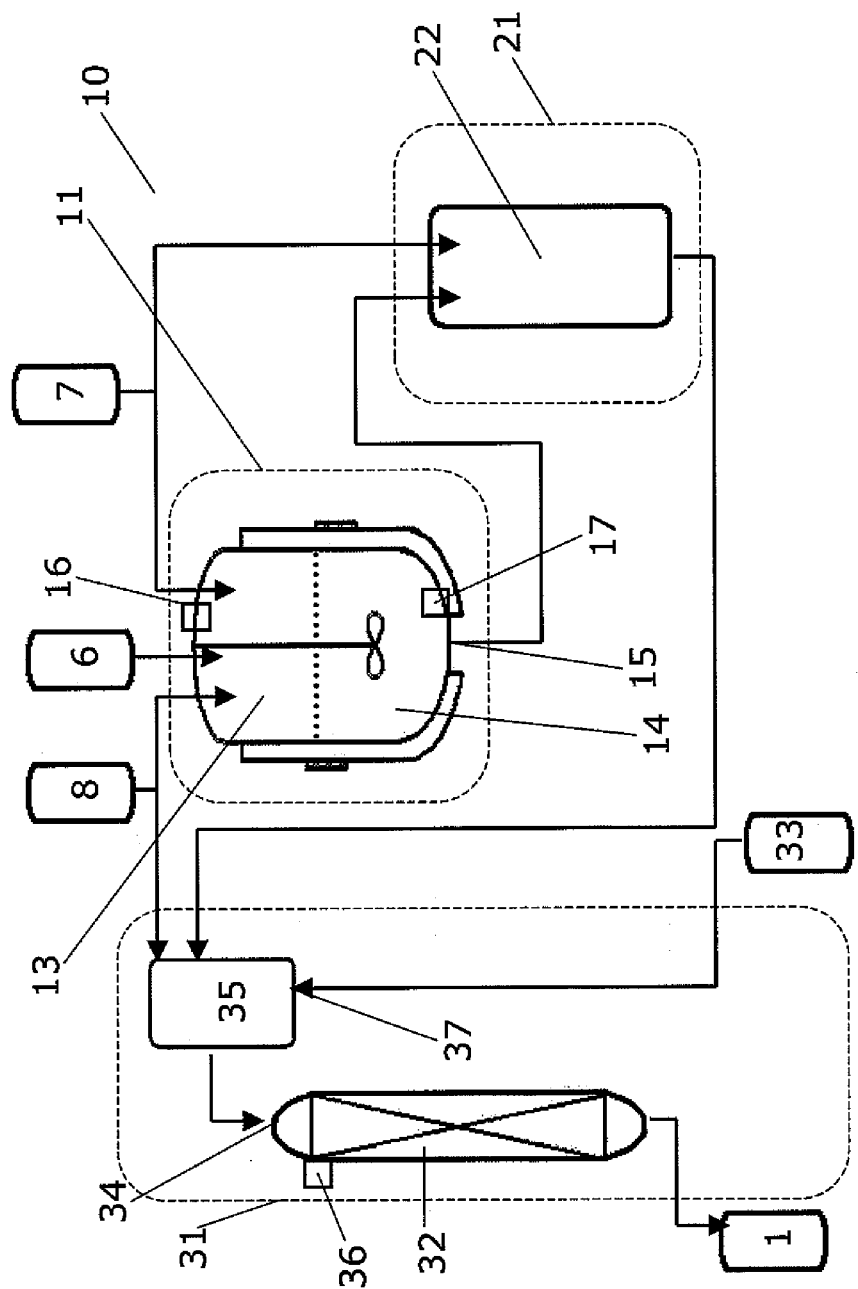
FIG. 2 is a schematic type drawing illustrating an apparatus used in the inventive synthesis reaction.

Referring now to FIG. 2. there is shown an apparatus (10) in which the alkylated quaternary amine salt product (QAP) (1) is continuously produced. The apparatus (10) as a whole comprises three sections: a reaction and phase-separation section (11), a post-heat section (21), and a stripping section (31). The starting materials (TAS, an alkylating agent, and water) are added via sources.

In the reaction section (11), TAS is continuously added via a TAS source (6). An alkylating agent is added to the reactions section (11) via an alkylating agent source (7) and water is added via a water source (8). These starting materials are continuously fed into a CSTR (12) as needed.

Within the CSTR (12) as the starting materials react, an environment comprising two liquid phases is formed. The light phase (13) is predominantly comprised of the reagents, TAS and alkylating agent. The dense phase (14) comprises predominantly QAP product within a concentrated aqueous solution.

In at least one embodiment, this two liquid phase environment is achieved by imposing specific reaction conditions within the CSTR (12). The pressure in the CSTR (12) is maintained at 30-100 psi. The temperature in the CSTR (12) is maintained at 40-60° C. The starting materials provide a residence time of between 30-120 minutes. Water comprises about 10 to less than 20 weight % of the starting materials added to the CSTR (12) (which is far less than the 20% that the QAP will ultimately be dissolved within). In some embodiments, the water comprises between 10 and 16 weight %. The ratio of light phase (13) to the dense phase (14) is maintained at a stable and desirable proportion, such as 1:4, as measured by sampling the lower portion of the CSTR under agitation.

These conditions cause the product QAP to form readily and to contain few impurities. The low amount of water added to the reactor allows the desired reaction to occur at a rapid rate and promotes the two solution phases to form in the CSTR and to separate readily. The low water level also slows down the rate of formation of undesirable impurities via unwanted hydrolytic side reactions. Because this environment allows for a rapid rate of QAP formation and a relatively slow rate of impurity formation, it results in the formation of a relatively high purity QAP with few impurities.

As a continuous reaction, starting materials are continually added to the CSTR (12), while a product-containing stream is constantly being removed from the CSTR (12). A novel aspect of this invention is that the reaction section functions as a separation device as well as a reaction device, so that only the dense-phase (14) is continuously removed. In this way, the reactant concentration can be held high in the CSTR to maximize the reaction rate, while the exiting stream is enriched in product and contains only low amounts of reactants. In at least one embodiment, the product exit (15) is located substantially at the bottom of the CSTR (12) to take advantage of the fact that the CSTR can be made to operate so that only the dense phase is present at this location. This is because there is less shear induced mixing at the bottom of the reactor, so that some of the dense phase tends to separate from the light phase and settle out at that location.

In at least one embodiment, other or additional mechanisms are used to separate and remove the dense phase from the CSTR (12), optionally using devices located outside and/or attached to the CSTR. These include and are not limited to, a vertical standpipe at the bottom of the CSTR (12), a baffle, weir, or other mechanism that provides time for the phases to undergo density induced separation, and any combination thereof. In at least one embodiment, sampling equipment (16, 17) is located at the top and/or bottom of the CSTR and is used to ascertain the contents of the two liquid phases.

In at least one embodiment, the starting materials input continuously to the CSTR comprise 10-16 weight % water. This critical amount of water promotes the formation and separation of the desired two liquid phases in the CSTR, while minimizing the amount of undesired hydrolytic byproducts in the product.

After it is removed from the CSTR (12), the dense phase is passed to the post heat section (21). In the post heat section, residual levels of the unreacted TAS is converted into QAP. In at least one embodiment the post heat section (21) comprises of a plug flow reactor (22). In at least one embodiment the plug flow reactor (22) is maintained at a temperature range of 50-70° C. and the dense phase is provided a residence time of 0.5-1.5 hours. In at least one embodiment, additional alkylating agent is fed into the post heat section (21) to further assure that sufficient alkylating agent is present to react with all of the remaining TAS.

After treatment, the product of the post heat section (21) is passed on to a stripping section (31). There any unreacted alkylating agent is stripped away and all that remains in the product is QAP as virtually all of the TAS has been reacted. The stripping section (31) comprises one or more tanks such as tank (32), which is in fluidic communication with a gas source (33). In at least one embodiment the fluidic communication is in liquid-gas kinetic equilibrium. The gas source (33) allows the gas to flow over the product, which depurates/removes any remaining alkylating agent from the product. In at least one embodiment, the gas used includes but is not limited to air, nitrogen, argon or any combination thereof. In at least one embodiment, the gas flows in a countercurrent manner to the product.

In at least one embodiment the tank is a flash tank or flash drum. In at least one embodiment, the product of the post heat section passes into a flash tank/flash drum (35) before being passed onto the tank (32). In at least one embodiment the gas inlet (37) is positioned at the bottom of the flash tank/flash drum. Positioning at the bottom allows it to be submerged in liquid and better facilitate the gas purge In at least one embodiment the tank (32) is a stripping column. The stripping column comprises a plurality of column internals such as packing, trays, baffles, wiers or a combination of thereof, which cause an increase in the interfacial area for vapor-liquid contact.

In at least one embodiment, the product inlet (34) is located at the top of the tank (32). In at least one embodiment, the stripping section (31) reduces the amount of alkylating agent to less than about 100 ppm in the product. After a highly pure QAP (1) is produced, additional water is added to obtain a QAP solution that contains about 20 weight % water (the additional water is added after the post-heat section, and before or during the stripping section). In at least one embodiment, the tanks (32 or 35) in the stripping section (31) may also be vented using pressure release valves (36).

While this method does continually produce high quality QAP, the ultimate purity of the QAP is also dependent on the quality of TAS input into the apparatus (10). Unfortunately, some TAS and DMAEA in particular, have short shelf lives and the QAP produced (and DMAEA.MCQ in particular) from poor-quality TAS (and DMAEA in particular) have been observed to result in degraded QAP quality. In at least one embodiment, after the QAP has been produced, a stabilizing additive is added to the QAP containing solution. Previously, MEHQ and copper have been used a stabilizer for DMAEA. Unfortunately MEHQ is not ideal as it has compatibility problems with downstream chemicals used in polymerizing the QAP, is expensive, and causes unwanted side reactions with copper.

In at least one embodiment, the added stabilizing additive is BHT. In at least one embodiment, BHT is combined with copper. BHT is less expensive than MEHQ, is chemically compatible with downstream polymerization chemicals, and does not react with copper. The use of BHT allows the produced QAP to reside in a high water (20%) solution without degrading over time. In at least one embodiment a combination of BHT, MEHQ, and copper are used together to stabilize the QAP.

EXAMPLES

The foregoing may be better understood by reference to the following example, which is presented for purposes of illustration and is not intended to limit the scope of the invention.

A pilot plant unit was assembled to demonstrate the process and to obtain comparative data. Using the process equipment described above, the process was repeatedly executed in successive experiments. Each experiment used a specific set of conditions and was run for a period of time long enough to reach steady-state conditions. In addition to sampling the final product, an in-process sample was also taken from the lower portion of the CSTR by means of a dip-tube installed in the CSTR, in order to observe the physical state of the reaction mixture in the lower portion of the reactor at any given time.

The final product was analyzed for the impurities acrylic acid (AA), N,N-dimethylaminoethyl acrylate (DMAEA), and N,N-dimethylaminoethanol (DMAE). The level of acrylic acid impurity in the final product is commonly measured to give an indication of the level of acrylate ester hydrolysis over the course of the entire process. Also measured were the total amine impurities (DMAEA+DMAE), which indicate the total level of TAS present in the final product. These amine impurities are primarily generated in the CSTR or reaction section of the process, where they arise from hydrolytic side reactions that ultimately form DMAEA and DMAE salts that are unreactive towards the desired quaternization reaction. We have discovered that the amount of these total amines (DMAEA and DMAE) is an important indicator of the quality of the final product, as these amine impurities cause the final product to be unstable towards polymerization during processing and storage.

As shown in table 1, control runs 1 and 4 gave unacceptably high levels of residual acrylic acid and unquaternized amine impurities. In contrast, run 11 provided extremely low levels of unquaternized amine impurities in the final product, while also providing low levels of acrylic acid impurity. Runs 9 and 10B, provided reasonably low levels of acrylic acid and unquaternized amine impurities in the final product, but the impurity levels were higher than those provided by run 11.

TABLE 1

| Experiment Run # | CSTR Operating Conditions (at 50° C./60 psi) | | | Final Product Impurities (ppm) | |
|---|---|---|---|---|---|
| | Residence Time (min) | Water Added (wt. %) | Physical State | Acrylic Acid | DMAE + DMAEA |
| 1 | 60 | 20 | One-phase | 3,230 | 5,600 |
| 4 | 50 | 17 | One-phase | 1,848 | 3,240 |
| 11 | 75 | 13.3 | Two-phase | 770 | <300 |
| 9 | 60 | 15.5 | Two-phase | 930 | 1669 |
| 10B | 75 | 15.5 | Two-phase | 883 | 1447 |

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), end ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of continuously producing QAP comprising the steps of:
    continuously feeding reactants into a CSTR, the reactants comprising TAS, water, and an alkylating agent;
    maintaining conditions in the CSTR such that the pressure in the CSTR remains at 30-100 psi and also such that two distinct liquid phases form, a dense phase comprising more than 80% QAP and less than 20% water, and a light phase, present at greater than about 5 wt.% of the reaction mixture, comprising TAS, and alkylating agent, the dense phase being positioned below the light phase;
    not allowing the water content of the CSTR to exceed 16% of the reactants continuously added to the CSTR; and
    separating TAS from QAP within the CSTR while the TAS is reacting with the alkylating agent by continuously removing dense phase liquid from the CSTR, wherein the reactants are fed into the reactor from above the light phase, wherein the reactants form the QAP in the light phase, wherein the produced QAP migrates down into the dense phase, wherein at least a portion of the dense phase undergoes lower shear forces than the shear forces present in the light phase, and wherein the removed dense phase comprises more ppm of QAP than ppm of impurities, said impurities comprising unquaternized amines and acrylic acid, wherein the produced QAP has less than 300 ppm of TAS within it.

2. The method of claim 1 wherein the TAS is selected from the group consisting of DMAEA, any n,n-dialkylaminoalkyl (meth)acrylates, (meth)acrylamides, and any combination thereof.

3. The method of claim 1 wherein QAP produced is DMAEA.MCQ.

4. The method of claim 1 in which the alkylating group is selected from the group consisting of: methyl chloride, benzyl chloride, cetyl chloride, dimethyls sulfate, and any other commonly known alkylating agent, and any combination thereof.

5. The method of claim 1 in which the dense second phase is removed from the CSTR from the bottom of the CSTR.

6. The method of claim 1 in which additional reaction of residual TAS in the removed dense phase liquid is facilitated by reacting it in a plug flow reactor.

7. The method of claim 1 in which additional reaction of residual TAS in the removed dense phase liquid is facilitated by adding additional alkylating agent.

8. The method of claim 1 in which the alkylating agent is removed by purging the dense phase liquid with a gas flow.

9. The method of claim 1 in which the alkylating agent is removed by passing it through a stripping column.

10. The method of claim 1 in which the alkylating agent is removed by passing it into the top of a stripping column and passing a gas into the bottom of the stripping column, the gas selected from the list consisting of air, nitrogen, and any combination thereof.

11. The method of claim 1 in which the temperature in the CSTR is maintained at between 40-60 ° C.

12. The method of claim 1 in which the residence time in the CSTR ranges between 30-120 minutes.

13. The method of claim 1 in which the ratio of light first phase to dense phase is maintained at between 1:1 and 1:20.

14. The method of claim 1 in which the dense phase liquid is removed from the bottom of the CSTR at a location in which shear induced mixing of TAS and QAP is low relative to other locations within the CSTR.

15. The method of claim 1 further comprising the step of adding BHT and copper to the produced QAP.

16. The method of claim 15 further comprising the step of adding MEHQ to the produced QAP.

17. The method of claim 1 further comprising the steps of:

facilitating the reaction of any residual TAS in the dense phase liquid;

stripping the alkylating agent from the dense phase liquid; and adding water to the dense phase liquid to obtain desired physical properties.

* * * * *